United States Patent [19]

Hjertman et al.

[11] Patent Number: 5,435,076
[45] Date of Patent: Jul. 25, 1995

[54] INJECTION DEVICE

[75] Inventors: Birger Hjertman, Vällingby; Gustav Levander, Bromma; Olle Ljungquist, Täby, all of Sweden

[73] Assignee: Pharmacia Aktiebolag, Sweden

[21] Appl. No.: 142,408
[22] PCT Filed: Apr. 16, 1993
[86] PCT No.: PCT/SE93/00336
    § 371 Date: Nov. 24, 1993
    § 102(e) Date: Nov. 24, 1993
[87] PCT Pub. No.: WO93/20869
    PCT Pub. Date: Oct. 28, 1993

[30] Foreign Application Priority Data

Apr. 21, 1992 [SE] Sweden .................. 9201247

[51] Int. Cl.⁶ .................. A61M 5/31; F26B 5/06
[52] U.S. Cl. .................. 34/296; 206/219;
                                53/310; 604/191; 604/416
[58] Field of Search ............ 206/219, 528, 438, 524.1,
    206/221, 828; 53/111 R, 285, 510, 127, 237,
    440; 604/191, 416; 34/296–297, 92, 285, 287,
                                284

[56] References Cited

U.S. PATENT DOCUMENTS

| | | | |
|---|---|---|---|
| 2,494,456 | 1/1950 | Still | 206/219 |
| 3,314,563 | 4/1967 | Mounier | 604/416 |
| 4,240,566 | 12/1980 | Bergman | 222/135 |
| 4,286,389 | 9/1981 | Ogle | 34/285 |
| 4,645,073 | 2/1987 | Homan | 206/219 |
| 4,941,876 | 7/1990 | Meyer et al. | 604/89 |
| 4,982,769 | 1/1991 | Fournier et al. | 141/98 |
| 5,184,450 | 2/1993 | Galy et al. | 53/440 |

Primary Examiner—Henry A. Bennet
Assistant Examiner—William C. Doerrler
Attorney, Agent, or Firm—Pollock, Vande Sande & Priddy

[57] ABSTRACT

A device for an injection apparatus, including a dual-chamber injection cartridge. The cartridge includes a front end, a rear end, a front opening in the vicinity of a front end of the cartridge, a front chamber located in the vicinity of the front opening and including a drug freeze-dried in the front chamber, a rear chamber including a liquid component, a movable wall separating the front chamber and the rear chamber, a bypass for transferring the liquid component between the front chamber and the rear chamber, and a rear piston. The cartridge is slidably arranged within a cylindrical sleeve substantially the same length as the cartridge. A stopper is located in the vicinity of the front opening of the cartridge. The stopper is directed rearwardly coaxially with the cartridge, wherein as the sleeve is displaced rearwardly after the freeze-drying of the drug, the stopper enters the front opening of the cartridge to sealingly close the cartridge. An actuator for actuating the rear piston may be attached in the vicinity of the rear end of the cartridge.

17 Claims, 5 Drawing Sheets

FIG. 5      FIG. 6

INJECTION DEVICE

FIELD OF THE INVENTION

The present invention relates to a device to be used in the preparation of injection solutions. More specifically, the invention relates to a device to be used in the preparation of injection solutions in dual-chamber type injection cartridges.

BACKGROUND OF THE INVENTION

Injection cartridges of the dual-chamber type are well-known and have found a wide use. They are used together with various types of injection apparatuses which serve to hold the cartridge as it is readied for injection and as injections are subsequently administered.

Injection cartridges of the dual-chamber type generally comprise a cylindrical barrel, which is shaped like a bottleneck at its front end and has an open rear end. The front end is closed by a septum of rubber or other suitable material, which is secured in place by means of a capsule. This capsule has a central opening where the septum is exposed and may be pierced by a hollow needle to establish a connection with the interior of the cartridge.

The rear end of the cartridge barrel is closed by a piston, which may be moved forward.

The cartridge is divided into two chambers by a transversal movable wall, which seals against the interior wall of the cartridge. The front chamber usually contains a solid component of the injectable preparation, while the rear chamber contains a liquid component, which is to dissolve or disperse the solid component. Through a bypass conduit arranged in the wall of the cartridge, the liquid in the rear chamber may be made to flow over into the front chamber when the movable wall is in a predetermined position.

The design and function of dual-chamber injection cartridges is well-known to those skilled in the art, and need not be described here in closer detail. In the manufacture of dual-chamber injection cartridges, the movable wall is first placed in a predetermined position in a cartridge barrel, which has been cleaned and silicone treated. The cartridges are then placed with their front ends upward, and a solution of the solid component of the injectable preparation is filled into the front chamber. The cartridges are then placed in a freeze-drying apparatus, and the solvent, which is usually water, is evaporated. After this, the cartridges are taken out from the freeze-drying apparatus, and their front openings are sealed by means of the septum and the capsule. When the front openings of the cartridges have been sealed, the rear chambers of the cartridges are filled with the liquid component of the injectable preparation, and the rear openings are sealed by means of the rear piston. This process has a number of drawbacks. The active agents are often sensitive to oxidation, which may occur when the cartridges are taken out from the freeze-drying apparatus to be sealed. Such an oxidation may lead to a degradation of the active agent of the injectable preparation. This is of special importance when the active agent is very expensive, such as growth hormones.

SUMMARY OF THE INVENTION

It would be very desirable to be able to seal the front chamber of the dual-chamber cartridges immediately after the freeze-drying process, without exposing the freeze-dried agent for the influence of atmospheric oxygen and other undesirable gases. However, this has been difficult with the equipment and processes used in the prior art, and practically impossible with cartridges which have a small volume.

However, by the use of the device and method of the present invention, the drawbacks mentioned above are largely eliminated. The device and method of the invention make it possible to freeze-dry a solution of the solid component in its chamber in the cartridge and subsequently to seal said chamber inside the freeze-drying apparatus without the freeze-dried component coming into contact with the outside atmosphere. At the same time, a safe seal of the cartridge is obtained. The seal comprises an area which may be pierced by a hollow needle for establishing a fluid connection with the interior of the cartridge.

According to the invention, a device is provided for an injection apparatus which comprises an injection cartridge of the dual-chamber type. The device comprises a cylindrical sleeve having substantially the same length as the cartridge. The sleeve is arranged slidably around the cartridge. The sleeve at its front end carries the stopper. The stopper is directed is directed rearward and is coaxial with the cartridge. The stopper, when the sleeve is moved rearward, enters the front opening of the cartridge to close it sealingly.

The device may at its rear end be provided with means for attaching actuating means for actuating the rear piston of the cartridge.

The sleeve is preferably arranged with a small spacing between its interior wall and the exterior wall of the cartridge, to provide a connection between the interior of the cartridge and the exterior environment. In another embodiment, this object is attained by providing openings in the wall of the sleeve near its front end.

Furthermore, the invention also provides a method for preparing injection apparatuses for injection cartridges of the dual-chamber type, wherein a solution or dispersion of the component which is to be the solid component in the cartridge is provided in the front chamber of each cartridge. The cartridge is inserted into a freeze-drying apparatus and subjected to a freeze-drying process. The cartridge is sealed while still remaining in said freeze-drying apparatus. What characterizes the process is that after each cartridge has been filled with the solution or dispersion, a device having a sleeve of the type previously described is arranged around each cartridge in such a way that its front end, with the stopper, is situated near the front opening of the cartridge. After a completed freeze-drying of the solution or dispersion, the sleeve with the stopper for each cartridge is moved rearward, such that the stopper is introduced into the front opening of the cartridge the cartridge to sealingly close the front opening.

Preferably, the freeze-drying process is carried out in the presence of a protective gas, such as nitrogen or argon, before the cartridges are sealed at their front ends.

BRIEF DESCRIPTION OF THE DRAWINGS

The invention will now be described in more detail, with reference to the accompanying drawings in which like parts have the same reference numbers. In the drawings.

DETAILED DESCRIPTION OF THE INVENTION

Figure 1:
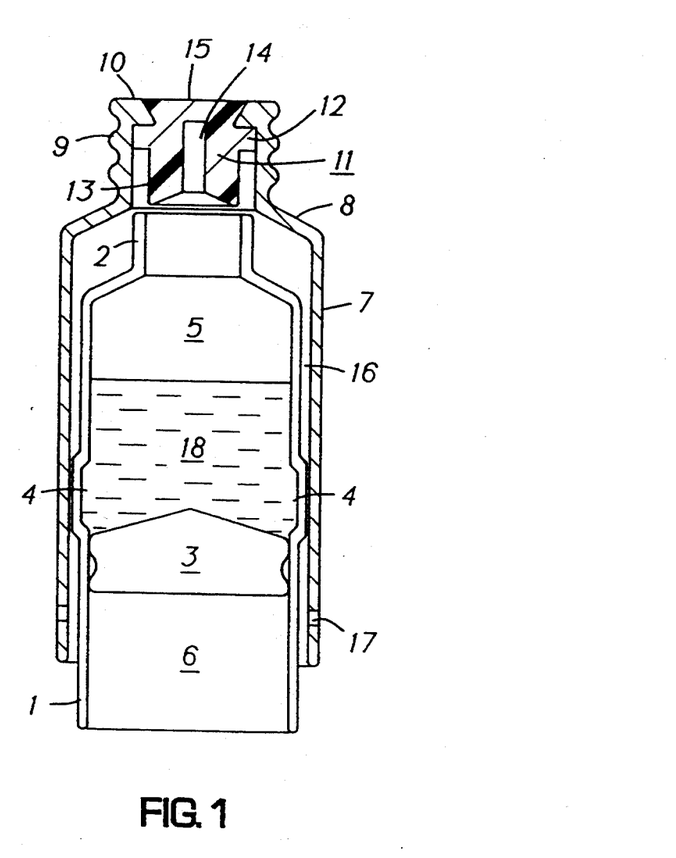
FIG. 1 shows a cross-sectional view of an embodiment of the device of the invention arranged around an injection cartridge before the freeze-drying process.

FIG. 1 shows a cross-sectional view of an embodiment of the device of the invention together with a dual-chamber injection cartridge before the freeze-drying process has been carried out. A dual-chamber injection cartridge has a barrel 1 and a forward neck portion 2. Inside the barrel is arranged the movable wall 3, just to the rear of the bypass arrangement 4. This bypass arrangement may be shaped as a conventional bypass channel in the wall of the barrel 1, but is preferably of a special design, which will be described in more detail later. The front chamber 5 of the cartridge is filled with a predetermined amount of a solution 18 of the component which is to be the solid component in the finished cartridge. Behind the movable wall 3, the rear chamber 6 is open to the atmosphere. This arrangement of a dual-chamber injecting cartridge before the freeze-drying is conventional and need not be described here in more detail.

According to the invention, the cartridge is surrounded by a sleeve 7, which has approximately the same length as the cartridge. At its front end 8, the sleeve is shaped to correspond with the forward neck portion of the cartridge. The sleeve 7 also has a further neck portion 9, which may be provided with a thread for securing an injection needle (not shown), and is terminated by an inward-directed flange 10. Inside the neck portion 9 of the sleeve is arranged a stopper 11, which has a flange 12. The flange 10 of the sleeve 7 and the flange 12 of the stopper 11 are arranged to cooperate to hold the stopper 11 securely in place inside the neck portion 9. The stopper 11 further has a rearwardly-directed cylindrical or slightly conical part 13, which is coaxial with the cartridge and its neck portion 2, and is dimensioned to fit sealingly inside said neck portion 2. The space between the interior surface of the neck portion 9 of the sleeve 7 and the surface of the cylindrical part 13 of the stopper 11 should be such that there is room for the neck portion 2 of the cartridge.

At its center, the stopper has a internal cavity 14, such that a thinner central part 15 is provided. This thinner part serves a septum, which may be penetrated by a hollow needle to afford a connection with the front chamber 5 after it has been sealed.

A small spacing 16 is arranged between the interior wall of the sleeve 7 and the exterior wall of the cartridge barrel 1. This spacing provides a passage for the vapor of the solvent, which is usually water, during the freeze-drying process. Such a passage may also be provided by the arrangement of openings (not shown) in the sleeve near its front 8.

The sleeve 7 is preferably transparent, or is provided with windows (not shown), so that it is possible to observe the cartridge and its contents.

At its rear end, the sleeve is provided with means 17 for attaching actuating means for readying the finished cartridge for injection, and possibly also for dispensing injections. These means 17 may be arranged as a thread or a part of a bayonet lock or snap lock or the like. Some examples of such arrangements will be shown later.

Figure 2:
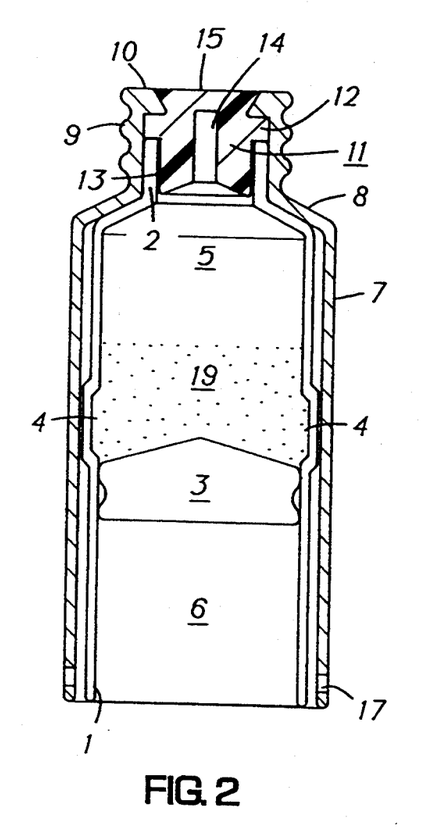
FIG. 2 shows a cross-sectional view of the embodiment shown in FIG. 1 after the freeze-drying has been completed and the front end of the cartridge has been sealed.

FIG. 2 shows the device of the invention after the freeze-drying process has been completed and the front chamber of the cartridge has been sealed. The liquid has now been evaporated, and a dry powder 19 remains of the solid component of the composition to be injected. The sleeve 7 and the stopper 11 have then been displaced rearwards, such that the stopper has entered the neck portion of the cartridge to seal the front chamber 5 against the exterior.

Figure 3:
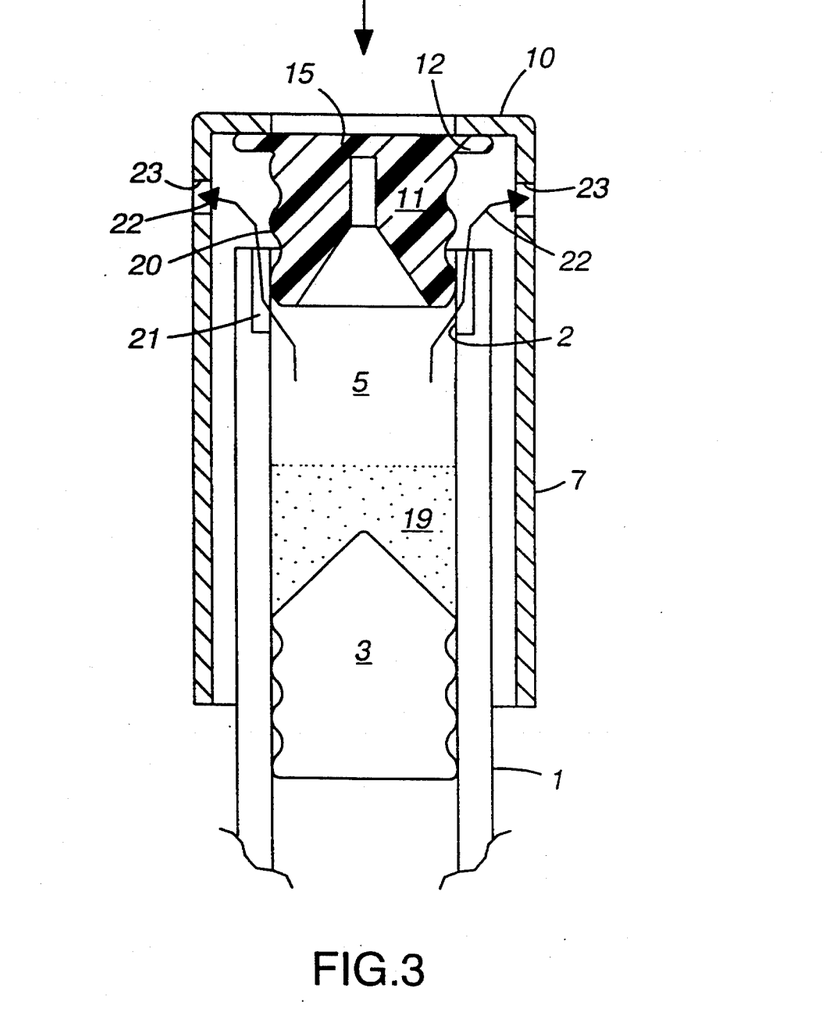
FIG. 3 shows a cross-sectional view of an embodiment of a modification of a stoppering arrangement according to the invention for the front end of the cartridge.

FIG. 3 shows, in a somewhat larger scale, a modification of the stopper arrangement. The stopper 11 is here provided with circumferential ridges 20 to give better sealing properties, and the rearmost part of it has been inserted into the neck 2 of the cartridge. The foremost part of the neck 2 is provided with surface modifications on its interior surface, such that the stopper 11 does not seal completely in this area. This makes it possible for solvent vapor to escape during the freeze-drying process, as is shown by the arrows 22, through holes 23 near the front end of the sleeve 7. On further movement of the stopper 11 rearward, the sealing ridges 20 will get into contact with the smooth part of the interior wall of the neck 2, to afford a complete sealing of the front chamber 5.

The advantage of this modification of the stopper arrangement is that the stopper is guided more securely into its sealing position inside the neck of the cartridge.

Figure 4:
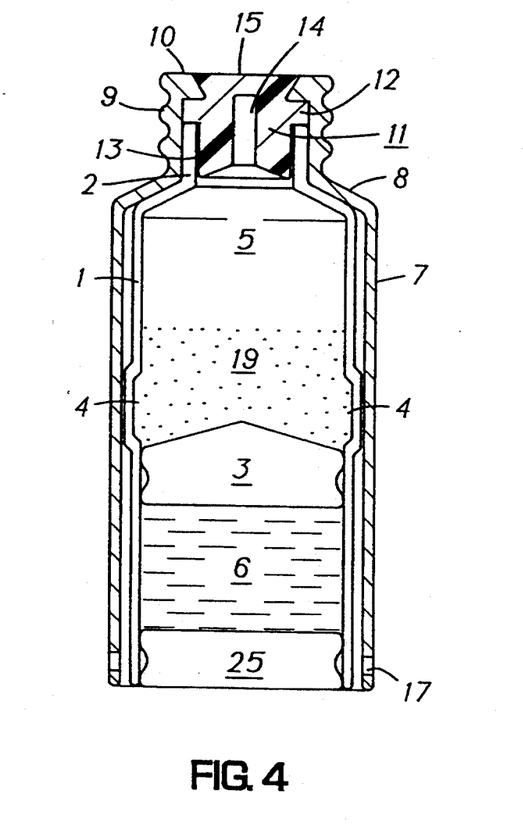
FIG. 4 shows a cross-sectional view of an embodiment of a finished cartridge after the liquid component has been added and the rear end of the cartridge has been sealed.

FIG. 4 shows the finished cartridge after the rear chamber 6 has been filled with the liquid component and the rear end of the cartridge has been closed by the piston 25. Actuating means for readying the cartridge for injecting may now be attached to the fastening means 17 near the rear end of the cartridge.

Figure 5:
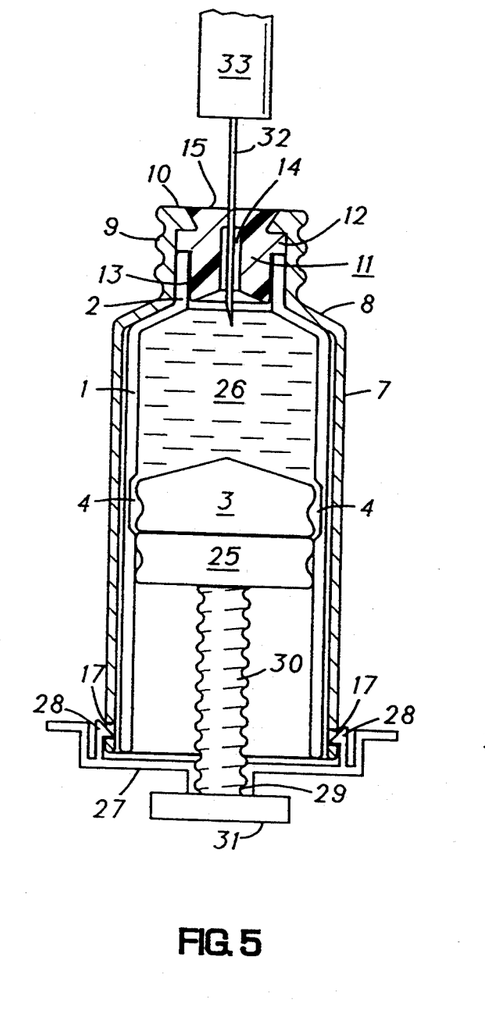
FIG. 5 shows a cross-sectional view of an embodiment of an arrangement of the device of the invention in the mixing of the two components.

FIG. 5 shows the device of the invention with a cartridge wherein the two components have been mixed to form a solution or dispersion 26. The rear piston 25 has been moved forward to urge the movable wall 3 to a position across the bypass means 4, and the liquid component has then been expelled from the rear chamber 6 into the front chamber 5 to form a solution or dispersion 26 with the solid component 19.

The forward movement of the rear piston 25 has been brought about by the movement of a screw 30 in a threaded hole 29 in a rear lid 27. This lid 27 has been fastened to the rear end of the sleeve 7 by means of snap fasteners 28 in the openings 17 at the rear end of the sleeve 7. Other means of fastening are also possible, such as a threaded connection or a bayonet lock.

In the embodiment shown in FIG. 5, it is not intended to administer injections directly from the cartridge. Instead, the cartridge is intended to be used as a kind of mixing vessel where the solid and liquid components are mixed in the way described, and the prepared solution or dispersion is then withdrawn by means of a hollow needle 32, which is inserted into the cartridge through the thin part 15 of the stopper 11 and which is attached to a syringe, which is shown schematically at 33. From this syringe 33, the ready-mixed injectable preparation may then be administered.

It is understood that when the mixed contents of the cartridge has been used up, the rear lid 27 with its snap fasteners 28 may easily be removed from the sleeve 7 and be attached to a fresh cartridge. For easy turning, the screw 30 is provided with a handle 31 at its rear end.

Figure 6:
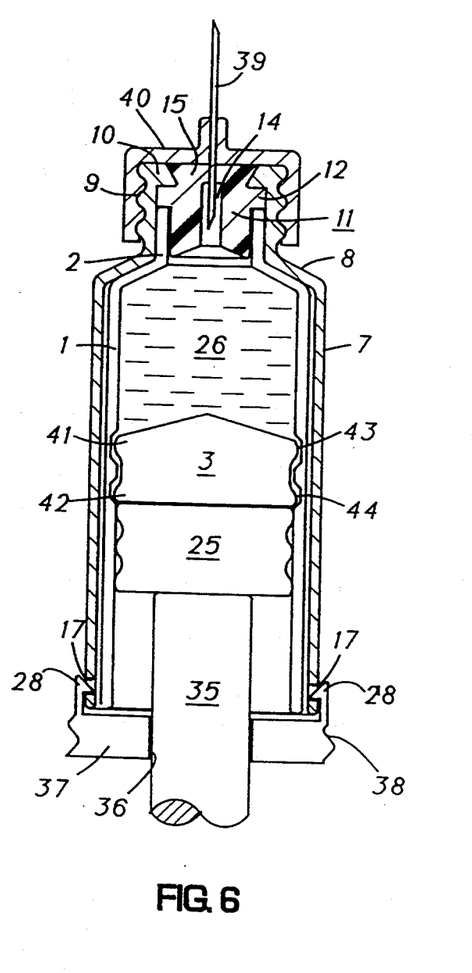
FIG. 6 shows a cross-sectional view of another arrangement for the same purpose.

FIG. 6 shows another embodiment of the device of the invention with a cartridge which has been readied for injection. In this embodiment, the rear piston 25 and the movable wall 3 have been brought forward by the action of a plunger 35, which is connected to a device for metering and administering injections (not shown). The plunger 35 is slidably arranged in an aperture 36 in a rear lid 37. The rear lid is fastened to the rear end of the sleeve 7 by means of snap fasteners 28 in the openings 17, as shown in FIG. 5. The rear lid 37 may be provided with a thread 38 for attaching the device for metering and administering injections.

In the embodiments shown in FIG. 6, it is intended to administer injections directly from the cartridge. A hollow needle 39 has therefore been made to penetrate the thin portion 15 of the stopper 11 to afford a liquid connection with the injectable preparation 26 in the cartridge. The hollow needle 39 is mounted in a threaded cap 40, which may be screwed onto the threaded neck 9 of the sleeve 7. At its front end, the hollow needle 39 is either pointed for a direct injection, or it is connected to a tube, which in its turn is connected to an injection needle.

Thus, it will be seen that the same sleeve device of the invention together with the cartridge may be attached to different devices for preparing and administering the injectable preparation. This is an important advantage of the present invention.

The connection between the sleeve and the devices for preparing and administering the injectable preparation may also be arranged according to a mechanical code, such that only a predetermined sleeve with cartridge will be attachable to the preparing and administering device. This will prevent that the wrong cartridge is attached, so that the risk that the patient gets a wrong dose is eliminated. Such a mechanical code may be established by a suitable arrangement of the snap locks and the openings in the sleeve.

In FIG. 6 is also shown an especially advantageous form of the bypass arrangement around the movable wall 3. In this embodiment, the movable wall 3 is provided with two circumferential sealing ridges 41 and 42, and the bypass connection is divided into two connections 43 and 44, which have the same spacing as the sealing ridges 41 and 42. In the initial stage, before the two components are mixed, the front sealing ridge 41 of the movable wall 3 seals against the part of the interior wall of the cartridge between the two connections 43 and 44, and the rear sealing ridge 42 hence seals against the interior wall of the cartridge to the rear of the rear connection 44. When the connection to the front chamber is to be established, the movable wall 3 will only have to be displaced the short distance necessary for the two sealing ridges 41 and 42 to rest against the connections 43 and 44, respectively. This shortened movement makes it possible to make the cartridge shorter, and also a shorter movement in the device for preparing and administering injections. This will result in a shorter overall design of the complete apparatus for injection, which is an important advantage in injection devices which are to be used by the patient himself for administering injections.

The bypass arrangement in the injection cartridges may be of the conventional type, with one or more by-pass channels in the wall of the cartridge. However, as such an arrangement will give a ridge in the exterior surface of the cartridge, this may give rise to positioning problems when it is desired that the sleeve 7 should fit snugly over the cartridge. The ridge or ridges in the exterior surface of the cartridge will mean that a sleeve has to be used which has an unduly great interior diameter, or which must be provided with an internal groove to accommodate the exterior ridge on the cartridge. This may also lead to difficulties in the correct guiding and positioning of the stopper 11 in the neck 2 of the cartridge.

However, in an especially preferred embodiment of the invention, this disadvantage will be eliminated. According to this embodiment, the bypass connection is not arranged as one or more channels, but as an area in the interior wall of the cartridge, which has been modified such that the movable wall does not seal completely against the interior wall in this area. Such a modification may be arranged as a pattern of unevennesses in the interior wall, such as shallow longitudinal grooves, possibly interrupted by peripheral grooves having the same depth. The depth of such grooves or other modifications may be between 0.06 and 0.6 mm, and will, therefore, not make necessary any external ridge on the cartridge. The number of grooves may be made sufficiently high to give at least the same flow capacity as a single channel and still guide the movable wall 3 properly inside the cartridge.

This arrangement of the bypass passages may also be divided into two or more areas to cooperate with a movable wall having circumferential sealing ridges, as has been described in the foregoing.

Furthermore, a preferred embodiment of this bypass arrangement is that the modified area or areas extend completely around the internal circumference of the cartridge. This gives an even flow of liquid, which aids in expelling dissolved gases and decreases the risk that sensitive compounds, such as growth hormones, are denatured in the mixing process. The function of the device of the invention in the manufacture of injection cartridges of the dual-chamber type will now be described in more detail, with reference to especially FIGS. 1 and 2 of the drawing.

In the initial stage, barrels 1 for injection cartridges are cleaned and siliconized, after which the movable wall 3 is inserted to a predetermined position in relation to the bypass arrangement 4. The front chamber 5 of the cartridges is then filled with a predetermined amount of a solution of the component which is to form the solid component of the injectable preparation. The filled cartridges are then placed with the front opening upwards in suitable trays for freeze-drying. These steps are conventional and the same as for prior art cartridges.

The sleeves 7 with the attached stoppers 11 are preferably mounted on trays. These trays are then arranged above the trays for the cartridges, such that the rear opening of the sleeves is facing downwards and each cartridge is inserted partly in a sleeve coaxially with the sleeve 7 and stopper 11. Through a spacing 16 between the cartridge and the interior wall of the sleeve 7, or openings in the wall of the sleeve near its front end, a connection for vapor is assured between the interior of the cartridge and the exterior of the sleeve 7, such that the contents of the cartridges may be freeze-dried.

The mounting of the sleeves 7 and the cartridges on trays serves to hold the sleeves and cartridges in correct positions relative to each other. When the trays are brought together after the freeze-drying, the stoppers 11 are guided into the necks of the cartridges. Small projections (not shown) may also be arranged on the interior wall of the sleeve 7 to aid in holding the sleeve and the cartridge in correct positions. Such projections should then preferably be resilient, so that they do not completely prevent the relative movement between the sleeve and the cartridge.

The complete arrangement of cartridges and sleeves with stoppers, each attached to its respective tray, is then introduced into a freeze-drying apparatus, and the freeze-drying process is carried out in a conventional manner. When the liquid phase of the solution has been evaporated, it is possible to introduce a protective inert gas in the freeze-dryer, such as nitrogen or argon. This gas will then constitute the gaseous phase in the sealed front chamber of the cartridges.

When the freeze-drying process is terminated, the front chambers of the cartridges are sealed by inserting the stoppers 11 in the necks 2 of the cartridges. This is carried out by bringing the two trays together, such that the sleeves 7 will guide the stoppers 11 into their correct places in the necks of the cartridges, to give a secure seal between the stoppers 11 and the necks 2 of the cartridges.

When the front chambers of the cartridges have been sealed, the cartridges are taken out from the freeze-drying apparatus, and the liquid component is filled into the cartridges through their rear ends, which are subsequently closed by means of the pistons 25. This is carried out in the conventional manner.

After this, the cartridges with their sleeves may be subjected to conventional post-treatment steps, such as sterilizing, labelling and packing. When the cartridges are to be readied for mixing of the components and injection, a suitable device for this, as described in the foregoing, is attached to the rear end of the sleeve, and the desired process is carried out.

The materials for the sleeve of the invention can easily be selected by persons skilled in the art. Various plastic materials have turned out to be suitable, such as polyolefins, halogenated polyolefins, polyamides, polyesters and polycarbonates. As mentioned in the foregoing, the sleeve should preferably be transparent or provided with windows, to permit observation of the cartridge and its contents.

Through the device of the present invention, it has become possible to freeze-dry the contents of dual-chamber injection cartridges and seal the cartridges without any risk that the contents will come into contact with atmospheric oxygen after the freeze-drying has been carried out. It is also possible to introduce an inert protective gas in the cartridges after the freeze-drying of the contents.

A further advantage of the sleeve of the invention is that it serves as protection against the explosion or bursting of the cartridge. This may occur if the liquid component is urged into the front chamber but no connection has been arranged between the front chamber and the outside atmosphere, for instance if the user has forgotten to insert a hollow needle through the stopper.

We claim:
1. A device for an injection apparatus, comprising:
   a dual-chamber injection cartridge, comprising:
      a front end and a rear end;
      a front opening in the vicinity of a front end of said cartridge;
      a front chamber located in the vicinity of said front opening and including a drug freeze-dried in said front chamber,
      a rear chamber including a liquid component,
      a movable wall separating said front chamber and said rear chamber,
      a bypass for transferring said liquid component between said front chamber and said rear chamber, and
      a rear piston;
   a cylindrical sleeve substantially the same length as said cartridge, said cartridge being slidably arranged within said sleeve;
   a stopper located in the vicinity of said front opening of said cartridge, said stopper being directed rearwardly coaxially with said cartridge, wherein as said sleeve is displaced rearwardly after the freeze-drying of said drug said stopper enters the front opening of said cartridge to sealingly close said cartridge; and
   means in the vicinity of said rear end of said cartridge for attaching means for actuating said rear piston.

2. A method for preparing an injection apparatus for dual-chamber injection cartridges, said method comprising the steps of:
   providing a device for an injection apparatus, the device comprising a dual-chamber injection cartridge, including a front end, a rear end, a front chamber, a rear chamber, a movable wall separating the front chamber and the rear chamber, a bypass for transferring material between the front chamber and the rear chamber, and a piston;
   providing a solution or dispersion of a component in a front chamber of the cartridge;
   arranging a cylindrical sleeve around the cartridge;
   providing a front end of the sleeve with a stopper, said stopper being directed rearwardly toward and coaxially with the cartridge;
   inserting the cartridge into a freeze-drying apparatus;
   subjecting the solution or dispersion of the component to a freeze-drying process, the freeze-drying process being carried out with the stopper in a position where a front opening of the cartridge is not sealed;
   displacing the sleeve and the stopper rearwardly such that the stopper is inserted into the front opening of the cartridge to sealingly close to cartridge;
   removing the sealed cartridge from the freeze-drying apparatus;
   providing a liquid component in the rear chamber of the cartridge; and
   providing the rear end of the sleeve with means for actuating the rear piston.

3. A device according to claim 1, characterized in that a spacing is arranged between the exterior wall of the cartridge and the interior wall of the sleeve, to afford a connection between the interior of the cartridge and the exterior environment.

4. A device according to claim 1, characterized in that openings are arranged in the sleeve near its front end, to afford a connection between the interior of the cartridge and the exterior environment.

5. A device according to claim 1, characterized in that the stopper is provided with sealing ridges which cooperate with an area in the interior wall of the cartridge near its front opening, such that the stopper does not seal completely against said area until the stopper is fully inserted.

6. A device according to claim 1, characterized in that the stopper is provided with a thinned central part, to serve as a septum for affording fluid contact with the sealed front chamber.

7. A device according to claim 1, wherein said bypass comprises an area of an interior wall of said cartridge, wherein said movable wall does not seal completely against said interior wall.

8. A method according to claim 2, wherein a protective gas is introduced into the freeze-drying apparatus before the cartridge is sealingly closed.

9. An injection apparatus, comprising:
a dual-chamber injection cartridge, comprising:
a front end and a rear end;
a front opening in the vicinity of a front end of said cartridge;
a front chamber located in the vicinity of said front opening and including a drug freeze-dried in said front chamber,
a rear chamber including a liquid component,
a movable wall separating said front chamber and said rear chamber,
a bypass for transfer,ring said liquid component between said front chamber and said rear chamber, and
a rear piston;
a cylindrical sleeve substantially the same length as said cartridge, said cartridge being slidably arranged within said sleeve;
a stopper located in the vicinity of said front opening of said cartridge, said stopper being directed rearwardly coaxially with said cartridge, wherein as said sleeve is displaced rearwardly after the freeze-drying of said drug said stopper enters the front opening of said cartridge to sealingly close said cartridge; and
means in the vicinity of said rear end of said cartridge for attaching means for actuating said rear piston.

10. An injection apparatus, prepared in accordance with claim 2.

11. A device according to claim 1, further comprising:
a spacing arranged between an exterior wall of the cartridge and an interior wall of the sleeve, said spacing providing a connection between an interior of the cartridge and an exterior environment.

12. A device according to claim 1, further comprising:
openings arranged in the sleeve in the vicinity of the front end, the openings providing a connection between an interior of the cartridge and an exterior environment.

13. A device according to claim 3, wherein the stopper includes sealing ridges that cooperate with an area in an interior wall of the cartridge in the vicinity of the front opening, such that the stopper does not completely seal said area until the stopper is fully inserted.

14. A device according to claim 4, wherein the stopper includes sealing ridges that cooperate with an area in an interior wall of the cartridge in the vicinity of the front opening, such that the stopper does not completely seal said area until the stopper is fully inserted.

15. A device according to claim 3, characterized in that the stopper is provided with a thinned central part, to serve as a septum for affording fluid contact with the sealed front chamber.

16. A device according to claim 4, characterized in that the stopper is provided with a thinned central part, to serve as a septum for affording fluid contact with the sealed front chamber.

17. A device according to claim 5, characterized in that the stopper is provided with a thinned central part, to serve as a septum for affording fluid contact with the sealed front chamber.

* * * * *